United States Patent [19]

Pitzele et al.

[11] Patent Number: 4,797,470

[45] Date of Patent: * Jan. 10, 1989

[54] N-TERMINALLY SUBSTITUTED TYROSYL ALANINE

[75] Inventors: Barnett S. Pitzele, Skokie; Donald W. Hansen, Jr., Chicago; Robert W. Hamilton, Wilmette; Daniel R. Pilipauskas, Glenview; Michael Clare, Skokie, all of Ill.

[73] Assignee: G. D. Searle & Co., Chicago, Ill.

[ * ] Notice: The portion of the term of this patent subsequent to Aug. 30, 2005 has been disclaimed.

[21] Appl. No.: 14,340

[22] Filed: Feb. 13, 1987

Related U.S. Application Data

[63] Continuation-in-part of Ser. No. 882,795, Jul. 14, 1986, Pat. No. 4,760,180, which is a continuation-in-part of Ser. No. 829,241, Feb. 14, 1986, abandoned, which is a continuation-in-part of Ser. No. 765,881, Aug. 14, 1985, abandoned.

[51] Int. Cl.⁴ .............................................. C07K 5/08
[52] U.S. Cl. .................................................... 530/331
[58] Field of Search .................. 530/302, 331; 514/19

[56] References Cited

U.S. PATENT DOCUMENTS

| | | | |
|---|---|---|---|
| 4,127,535 | 11/1978 | Coy et al. | 530/302 |
| 4,316,892 | 2/1982 | Jones | 530/302 |
| 4,407,746 | 10/1983 | Mazur et al. | 530/302 |
| 4,579,841 | 4/1986 | Stewart et al. | 514/19 |
| 4,603,121 | 7/1986 | Hansen, Jr. et al. | 530/302 |

*Primary Examiner*—Delbert R. Phillips
*Attorney, Agent, or Firm*—Frank P. Grassler; J. Timothy Keane; Paul D. Matukaitis

[57] ABSTRACT

This invention relates to compounds of the formula:

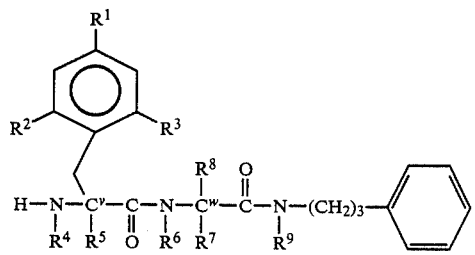

and the pharmaceutically acceptable acid addition salts thereof wherein $R^1$ is

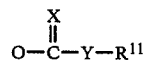

where X is oxygen or sulfur, Y is oxygen or nitrogen, and $R^{11}$ represents straight or branched chain lower alkenyl having 2-6 carbon atoms, or phenyl, benzyl, and their equivalents such as nitro, halogen, or lower alkyl or lower alkoxy substituted phenyl or benzyl; wherein $R^2$ and $R^3$ may be the same or different and represent straight or branched chain lower alkyl having 1-6 carbon atoms, wherein $R^4$–$R^9$ may be the same or different and represent hydrogen, or straight or branched chain lower alkyl having 1-6 carbon atoms; wherein $C_w$ is an asymmetric carbon atom when $R^7$ and $R^8$ are not the same and may be racemic or have the D or L configuration; and wherein $C^v$ is an asymmetric carbon atom and may be racemic or may have the D or L configuration.

The compounds of this invention are useful because they possess analgesic activity in mammals.

15 Claims, No Drawings

N-TERMINALLY SUBSTITUTED TYROSYL ALANINE

This application is a continuation-in-part of pending Ser. No. 882,795, filed July 14, 1986, now U.S. Pat. No. 4760180 which is a continuation-in-part of Ser. No. 829,241, filed Feb. 14, 1986, now abandoned, which is a continuation-in-part of Ser. No. 765,881, filed Aug. 14, 1985, also now abandoned.

BACKGROUND OF THE INVENTION

1. Field of the Invention

The present invention relates to novel substituted tyrosyl dipeptide amides. In particular, it provides novel tyrosyl dipeptide amides of Formula I which are useful as analgesic agents.

2. Prior Art

In 1975, a pentapeptide, methionine enkephalin, was reported by Hughes et al., *Nature*, 258, 577 (1975). This peptide is found in many areas of the brain where it appears to act as a neurotransmitter or neuromodulator in a central pain-supressant system. This naturally occurring peptide binds stereospecifically to partially purified brain opiate receptor sites. See for example Bradberry et al., *Nature*, 260, 793 (1976). It is also highly active in bioassays for opiate activity but exhibits only weak, fleeting analgesic activity when injected directly into the brain of the rat. See for example Belluzi et al., *Nature*, 260, 625 (1976).

In order to overcome the lack of in vivo activity, a number of investigators have made numerous modifications in the methionine enkephalin structure, such as substituting the glycine in the 2-position with a D-amino acid, N-methylation of the L-tyrosine, substituting the 4-phenylalanine with, for example, methyl or halo, modifying the C-terminus, etc., to produce enkephalin derivatives of varying properties and potencies.

Kiso, et al., *Peptide Chemistry* 1981, 65–70, Protein Research Foundation, Osaka, Japan (1982), disclosed the synthesis and activity of short chain enkephalin-like peptides, among them tripeptide and dipeptide alkylamides such as N-methyltyrosine-(D)-methionine sulfoxide-glycine-methylphenethylamide and tyrosine-(D)-methionine sulfoxide-phenylpropylamide.

Vavrek, et al., *Peptides* 2, 303, 1981, disclosed analog of enkephaline, among them the dipeptide tyrosine-D-alanine-phenylpropylamide, (Tyr-(D)Ala-PPA).

Hansen, et al., U.S. Pat. No. 4,599,325, which issued July 8, 1986 to the inventors of the present invention, discloses tyrosyl dipeptide amides possessing analgesic activity in mammals.

The compounds of this invention have unexpected and surprising superior properties when compared to the Vavrek, et al. compounds. The present invention provides new dipeptide derivatives which show improved potency as analgesic agents by both oral and parenteral routes of administration. Additionally, U.S. Pat. No. 4,316,892 relates to certain derivatives of methonine enkephalin derivatives useful as analgesic agents.

SUMMARY OF THE INVENTION

This invention encompasses analgesic tyrosine derivatives of Formula I:

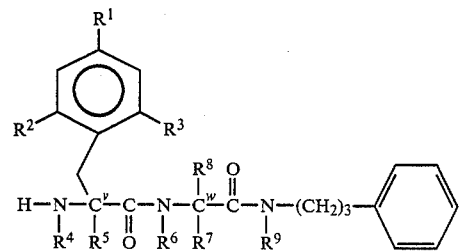

and the pharmaceutically acceptable addition salts thereof, wherein $R^1$ is

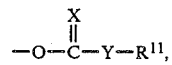

where X is oxygen or sulfur, Y is oxygen or nitrogen, and $R^{11}$ represents straight or branched chain lower alkenyl having 2–6 carbon atoms, or phenyl, benzyl, and their equivalents such as nitro, halogen, lower alkyl, or lower alkoxy substituted phenyl or benzyl;

wherein $R^2$ and $R^3$ may be the same or different and represent straight or branched chain lower alkyl having 1–6 carbon atoms;

wherein $R^4$–$R^9$ may be the same or different and represent hydrogen or straight or branched chain lower alkyl having 1–6 carbon atoms;

wherein $C^W$ represents an asymmetric carbon atom when $R^7$ and $R^8$ are not the same and may be racemic or have the D or L configuration; and wherein $C^v$ represents as asymmetric carbon atom that may be racemic or that may have the D or L configuration.

BRIEF DESCRIPTION

The compounds described in this invention are prepared according to the reaction sequence outlined in Scheme I. In Scheme I, an amino acid derivative (X) of known configuration which has its amino group blocked by "Z," is transformed into a mixed anhydride by reaction with isobutylchloroformate (IBCF) in the presence of N-methylmorpholine (NMM). The mixed anhydride is then coupled to the amino group of 3-phenyl-1-propamine to form an amide linkage. The amino blocking group, t-butoxycarbonyl (Boc), is then removed by hydrolysis in 6N HCl/dioxane to provide the amino amide (XII). Similarly, a 2,6-dialkyl amino-blocked-D,L-tyrosine derivative (XIII) is transformed into a mixed anhydride by reaction with isobutylchloroformate and N-methyl-morpholine. The resulting mixed anhydride is then coupled with the amino group on the amino amide (XII) to produce a substituted tyrosyl dipeptide amide as a mixture of diastereomers (XIV).

The resulting pair of diastereomers can be separated by methods well known in the art, such as by chromatography, crystallization and the like, to produce the individual diastereomers. The resulting individual diastereomer, or even the diastereomeric pair is further reacted with a lower alkyl, an aryl, or a lower alkenyl substituted isocyanate compound such as n-butylisocyanate, benzyl-isocyanate, allylisocyanate and the like. Alternatively, the individual diastereomer or the diastereomeric pair is reacted with a similarly substituted chloroformate compound such as ethylchloroformate, phenylchloroformate, allylchloroformate and the like. The resulting individual diastereomer or the diastereomeric pair can then be deblocked by hydrolysis with 6N HCl/dioxane to produce the compounds of Formula I.

In Scheme I, the Z of compound X represents an amino blocking group such as t-butoxycarbonyl (Boc) or benzyloxycarbonyl. In sulfur containing X, the Z is preferably Boc, which can be removed by hydrolysis with 6N HCl/dioxane.

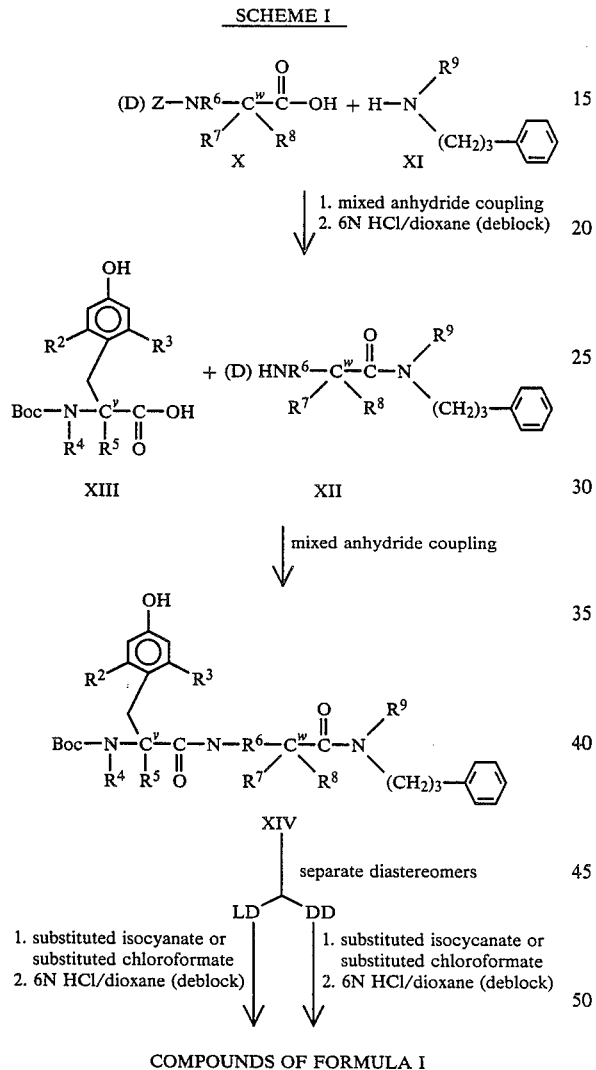

SCHEME I

COMPOUNDS OF FORMULA I

In this disclosure, by lower alkyl is meant straight or branched chain alkyl having 1-6 carbon atoms, such as methyl, ethyl, n-propyl, iso-propyl, n-butyl, iso-butyl, t-butyl, pentyl and the like. Similarly, by lower alkenyl is meant straight or branched chain alkenyl having 2-6 carbon atoms such as vinyl, allyl, 1-propenyl, 2-propenyl, 1-butenyl, 2-butenyl, 3-butenyl, and the like. By aryl is meant phenyl, benzyl, and contemplated equivalents of phenyl and benzyl such as nitro, carboxy, halogen, lower alkyl and lower alkoxy substituted phenyl or benzyl. By lower alkoxy, is meant an alkoxy wherein the alkyl group is straight or branched chain and having 1-6 carbon atoms.

Analogous to the enhanced analgesic properties of tyrosyl dipeptide amides already disclosed in our CIP series of co-pending applications (Ser. No. 882,795, filed July 14, 1986; Ser. No. 829,241, filed Feb. 14, 1986; and Ser. No. 765,881, filed Aug. 14, 1985), the dipeptide amides of the present invention possess unexpectedly superior analgesic activity over the enkephlin-like dipeptides disclosed by Vavrek, et al. More specifically, Ser. No. 882,795, of which this application is a continuation-in-part, discloses enhanced analgesic properties for compounds of the formula:

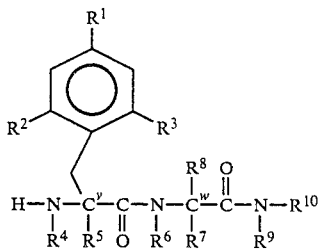

and the pharmaceutically acceptable acid addition salts thereof wherein $R^1$ is lower alkoxy or $-O-(CH_2)_n-$phenyl where the phenyl may be optionally substituted with halogen, $-NO_2$, $-CN$, $-NH_2$ or lower alkyl wherein n is 1 to 4; $R^2$ and $R^3$ represent lower alkyl, halogen, lower alkoxy or one of $R^2$ or $R^3$ is hydrogen and the other is lower alkyl, lower alkoxy, or halogen; $R^4$, $R^5$, $R^7$, $R^8$, and $R^9$ represent hydrogen or lower alkyl, $R^6$ represents hydrogen, lower alkyl, lower alkenyl, or $-(CH_2)_m-$cycloalkyl wherein m is 1 to 4 and the cycloalkyl has 3 to 8 carbon atoms; $R^{10}$ is $-(CH_2)_p-$phenyl wherein p is 1 to 4; and v represents an asymmetric carbon that may be racemic or have the D or L configuration; w represents an asymmetric carbon when $R^7$ and $R^8$ are not the same and may be racemic or have the D or L configuration. This invention also encompasses compounds where $R^1$ is hydroxy, provided at least one of $R^4$, $R^5$, $R^6$ or $R^9$ is lower alkyl.

The analgesic activity of the compounds of the present invention is demonstrated by their respective activities in the Writhing and Opiate Binding Assays. In some cases, the analgesic activity of the representative compounds was compared with that of a disclosed analog of enkephalin, (L)-tyrosine-(D)-alaninyl-phenylpropylamide.

Writhing Assay

Male Charles River albino mice (CD-1/HAM/1LR) weighing between 20 and 30 grams were used. Thirty minutes after subcutaneous or intragastric administration of a dose (0.1 mg/10 gram body weight) of the test compound, a 0.025% (w/v) phenylbenzoquinone solution was injected intraperitoneally (0.1 ml/10 gram body weight). Five minutes later, each mouse was placed in a large glass beaker and the number of writhes that occurred in the subsequent ten minutes was counted. A writhe consisted of dorsoflexion of the back, extension of the hind limbs, and strong contraction of the abdominal musculature. The test compound was considered to have produced analgesia in a mouse if the number of writhes elicited by phenylbenzoquinone was equal to or less than one-half the median number of writhes recorded for the saline-treated group that day. The results were expressed as the number of mice (out of a possible ten) in which the test compound produced analgesia. The test compound was rated active if the number of writhes in the drug treatment group was significantly less than the number of writhes in the saline treatment group as determined by a one-way analysis of variance. If the initial test done of 10 mg/kg inhibited writhing in greater than 6 of 10 mice, the effect of 5 additional doses was evaluated and an $ED_{50}$ value was calculated using a maximum likelihood function.

Opiate Binding Assay

The test compounds were evaluated from their ability to displace the binding of $^3$H-Naloxone to opiate receptors isolated from rat brain. Male rat [Crl: CD(SD) BR]obtained from Charles River Laboratories (Portage, MI) were sacrificed by cervical dislocation. A purified homogenate of receptor membranes was prepared from the brains according to the method described by Chang and Cuatrecasas. K.-J. Chang and P. Cuatrecasas. Multiple Opiate Receptors: Enkephalins, And Morphine Bind To Receptors Of Difference Specificity. *J. Biol. Chem.* 254, 2610–2618 (1979). The brains were homogenized in 10 volumes of 0.32M sucrose and centrifuged twice at 6,000 xg for 15 minutes. Following centrifugation of the supernatants at 40,000 xg for 30 minutes, the pellets were resuspended in 5 mM tris HCl and centrifuged at 6,000 xg. The supernatant was centrifuged at 40,000 xg. The resuspension in 5 mM tris and centrifugation was repeated twice. The final pellet was resuspended in 2 volumes of 50 mM tris HCl (pH 7.4). The homogenate was assayed for protein content according to the method of Itzhaki and Gill. R. F. Itzhaki and D. M. Gill, A Micro-Biuret Method For Estimating Proteins. *Anal. Biochem.* 9, 401–410 (1964).

The binding of the test compounds to the receptor membrane preparation was measured using a modification of the method of Pert and Snyder. C.B. Pert and S.H. Snyder, Properties Of Opiate-Receptor Binding In Rat Brain. *Proc. Natl. Acad. Sci.* 70, 2243–2247 (1973). The assay was run using a final concentration of 1 nM $^3$H-Naloxone and 0.5 mg/ml of homogenate protein. Levorphanol ($1 \times 10^{-5}$M) was used as the displacer for non-specific binding. The final concentration of the test compound was $10^{-5}$M. The assay was run in 0.05M tris HCl (pH 7.4). Total assay volume was 1.0 ml.

Samples were incubated at 24° C. for 60 min., filtered over Whatman GF/C glass fiber filters, and rinsed twice with 2.4 ml washes of ice-cold buffer. The filters were air dried at 50° C. for 30 min. After drying, 10 ml. of PCS was added to the vial and radioactivity determined using a Tracor Analytic Mark III liquid scintillation counter with a counting efficiency of 48%.

The $IC_{50}$ values, i.e., the concentration of the test compounds which inhibited $^3$H-Naloxone specific binding to the opiate receptor by 50%, were obtained from loglogit plots of concentration-response curves.

The compounds of the present invention as representated by Formula I can be administered in such oral dosage forms as tablets, capsules, pills, powders, granules, suspensions, or solutions. They may also be administered rectally or vaginally, in such forms as suppositories or bougies. They may also be introduced in the form of eye drops, or they may be administered intraperitoneally, subcutaneously, or intramuscularly, using forms known to the pharmaceutical art. In general, the preferred route of administration is oral.

An effective but nontoxic quantity of the compound is employed in treatment. The dosage regimen for preventing or treating symptoms by the compounds of this invention is selected in accordance with a variety of factors including the type, age, weight, sex and medical condition of the mammal, the severity of the symptoms, and the route of administration of the particular compound employed. A physician or veterinarian of ordinary skill will readily determine and prescribe the therapeutically effective dosage based on the route of administration of the analgesic agent to prevent or arrest the progress of the condition. In so proceeding, the physician or veterinarian could employ relatively low dosages at first, subsequently increasing the dose until a maximum response is obtained.

The compounds of Formula I can also be administered as pharmaceutically acceptable acid addition salts such as the hydrochloride, hydrobromide, hydroiodide, sulfate, phosphate, acetate, propionate, lactate, maleate, malate, succinate, tartrate and the like. Additionally, the compounds of this invention may be administered in a suitable hydrated form.

The compounds of this invention may be prepared by any number of methods known to those skilled in the art. For example, the particular sequence of reactions by which the individual amino acids are joined to form the compounds of Formula I is generally not of critical importance being chosen principally for convenience or for maximum yields. Moreover, the choice of activating reagents and conditions for joining amino acids or small peptides is not limited to those specifically described herein. The peptide intermediates and products of this invention are typically purified by crystallization or by column chromatography. Column chromatography also permits the separation of diastereomeric pairs into the individual diastereomers, thereby allowing one to employ a racemic amino acid as a starting material in the dipeptide synthesis.

The accompanying examples illustrate the methods used to prepare the compounds of this invention. These examples are given by way of illustration only and in no way should be construed as limiting the invention is spirit or in scope, as many modifications in materials and methods will be apparent from this disclosure to those skilled in the art.

DESCRIPTION OF THE PREFERRED EMBODIMENT

Example 1

Mixture of N-[(1,1-dimethylethoxy)carbonyl]-2,6-dimethyl-D-tyrosyl-N-(3-phenylpropyl)-D-alaninamide and N-[1,1-dimethylethoxy)carbonyl]-2,6-dimethyl-L-tyrosyl-N-(3-phenylpropyl)-L-alaninamide

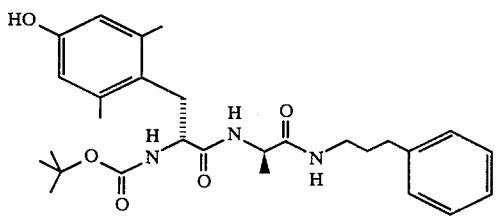

only DD is shown

The titled DD and LL enantiomeric pair are prepared according to Example 3 of U.S. Pat. No. 4,599,325 by substituting for racemic t-butylcarbonyl-2,6-dimethyltyrosine either its D or L enantiomer, wherein the D enantiomer is reacted with 3-phenylpropyl-D-alaninamide to produce the DD diastereomer, and wherein the L-enantiomer is reacted with 3-phenyl-propyl-L-alaninamide to produce the LL diastereomer.

Example 2

Mixture of N-[(1,1-dimethylethoxy)carbonyl]-2,6-dimethyl-O-[(phenylamino)carbonyl]-D-tyrosyl-N-(3-phenylpropyl)-D-alaninamide and N-[(1,1-dimethylethoxy)carbonyl]-2,6-dimethyl-O-[phenylamino)carbonyl]-L-tyrosyl-N-(3-phenylpropyl)-L-alaninamide

Example 3

Mixture of 2,6-dimethyl-O-[(phenylamino)carbonyl]-D-tyrosyl-N-(3-phenylpropyl)-D-alaninamide, monohydrochloride and 2,6-dimethyl-O-[(phenylamino) carbonyl]-L-tyrosyl-N-(3-phenylpropyl)-L-alaninamide, monohydrochloride.

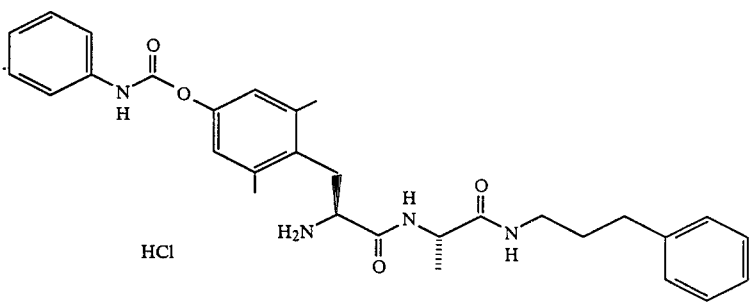

only LL is shown

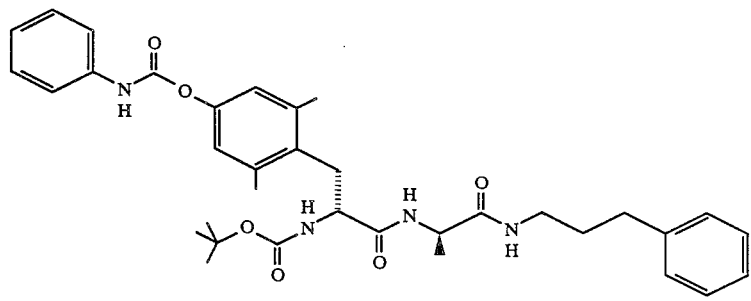

only DD is shown

To 15.0 g (30 mmol) of the product of Example 1 in 300 ml of benzene was added 6.6 ml (60 mmol) of phenylisocyanate plus 6 drops of triethylamine. This heterogeneous mixture was stirred at room temperature under argon for 4 days. The product, a white solid, was suction filtered from the reaction mixture and washed liberally with benzene, hexane, and diethyl ether. The product was then vacuum-dried to produce 14.6 g (79% yield) of the titled material.

Analysis for $C_{35}H_{44}N_4O_6$ (MW=616.76):

| | | | |
|---|---|---|---|
| Calcd: | C, 68.16; | H, 7.19; | N, 9.08. |
| Found: | C, 68.02; | H, 7.06; | N, 9.40. |

NMR shift of (D)Ala—$CH_3$ = 1.29δ(DMSO-$d_6$).

The product from Example 2 was dissolved in 30 ml of glacial acetic acid and treated with 8 ml of 6.8N HCl-dioxane. After 1.5 hr. of reaction at room temperature and under nitrogen, the mixture was stripped to a syrup. The syrup was dissolved in methanol, filtered, stripped, and triturated repeatedly with diethyl ether. The resulting solid was dried in a vacuum desiccator to give the hydrochloride product.

Analysis for $C_{30}H_{36}N_4O_4 \cdot HCl$ (MW=553.11):

| | | | | |
|---|---|---|---|---|
| Calcd: | C, 65.15; | H, 6.74; | N, 10.13; | Cl, 6.41. |
| Found: | C, 64.91; | H, 6.74; | N, 10.24; | Cl, 6.21. |

NMR shift for (D)Ala—$CH_3$=1.29δ($CD_3OD$).

Example 4

N-[(1,1-dimethylethoxy)carbonyl]-2,6-dimethyl-O-[(phenylamino) carbonyl]-D-tyrosyl-N-(3-phenylpropyl)-D-alaninamide.

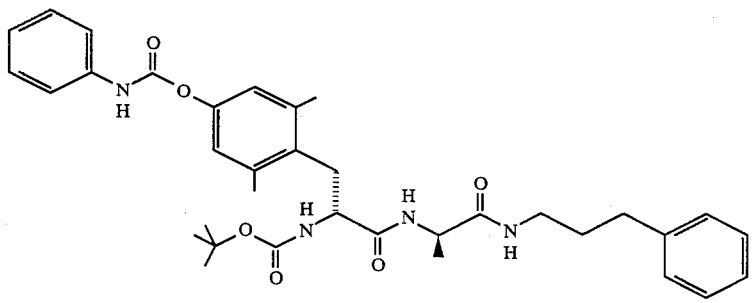

The title compound was synthesized by the method of Example 2 using the pure diastereomer, N-[(1,1-dimethylethoxy)carbonyl]-2,6-dimethyl-D-tyrosyl-N-(3-phenylpropyl)-D-alaninamide, in place of the enantiomeric pair of Example 1.

Analysis for $C_{35}H_{44}N_4O_6$ (MW=616.76):

| Calcd: | C, 68.16; | H, 7.19; | N, 9.08. |
|---|---|---|---|
| Found: | C, 68.17; | H, 7.09; | N, 9.08. |

NMR for (D)Ala—$CH_3 = 1.29\delta(CD_2Cl_2)$
$[\alpha]_D + 1.9°(CHCl_3)$.

Example 5

2,6-dimethyl-O-[(phenylamino)carbonyl]-D-tyrosyl-N-(3-phenylpropyl)-D-alaninamide, monohydrochloride.

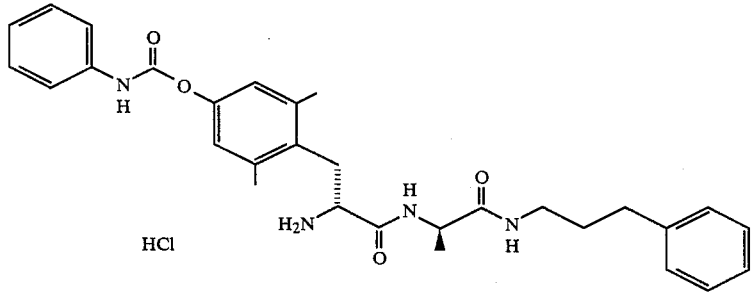

The product of Example 4 was dissolved in glacial acetic acid and reacted with 6.8NHCl-dioxane according to the procedure described in Example 3 to produce the titled hydrochloride.

Analysis for $C_{30}H_{36}N_4O_4 \cdot HCl \cdot \frac{1}{4}H_2O$ (MW=557.61):

| Calcd: | C, 64.62; | H, 6.78; | N, 10.04; | Cl, 6.35. |
|---|---|---|---|---|
| Found: | C, 64.56; | H, 6.70; | N, 10.07; | Cl, 6.35. |

NMR for (D)Ala —$CH_3 = 1.29\delta(CD_3OD)$
$[\alpha]_D - 68.8°(CH_3OH)$.

Example 6

O-[(butylamino)carbonyl]-N-[(1,1-dimethylethoxy)-carbonyl]-2,6-dimentyl-D-tyrosyl-N-(3-phenylpropyl)-D-alaninamide.

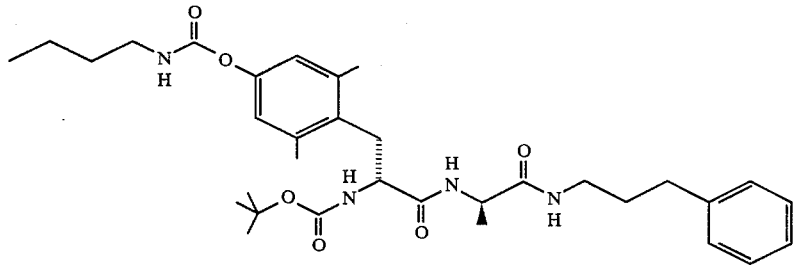

The title compound was prepared according to the method described in Example 2 using the pure diastereomer N[(1,1-dimethylethoxy)carbonyl]-2,6-dimethyl-D-tyrosyl-N-(3-phenylpropyl)-D-alaninamide, in place of its enantiomeric pair and n-butylisocyanate in place of phenylisocyanate. Unlike Example 2, the reaction was driven to completion by refluxing the reaction mixture for 4 days.

Analysis for $C_{33}H_{48}N_4O_6$ (MW=596.77):

| Calcd: | C, 66.42; | H, 8.11; | N, 9.39. |
|---|---|---|---|
| Found: | C, 66.45; | H, 7.80; | N, 9.44. |

NMR for (D)Ala—$CH_3 = 1.28\delta(CD_3OD)$
$[\alpha]_D - 5.0°(CH_3OH)$.

Example 7

O-[(butylamino)carbonyl]-2,6-dimethyl-D-tyrosyl-N-(3-phenylpropyl)-D-alaninamide, monohydrochloride.

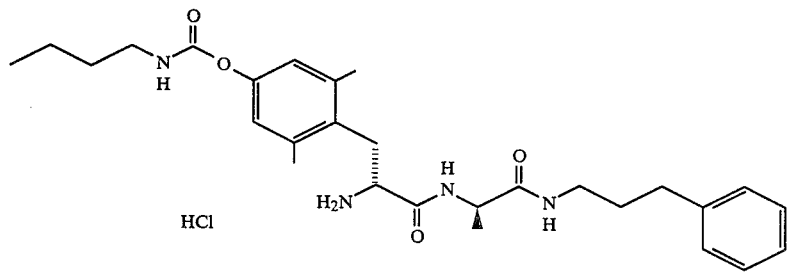

| Calcd: | C, 68.55; | H, 7.35; | N, 8.88. |
| Found: | C, 68.49; | H, 7.21; | N, 9.17. |

The title compound was prepared by reacting the product of Example 6 in glacial acetic acid with 6.8N HCl-dioxane according to the procedure described in Example 2.

Analysis for $C_{28}H_{40}N_4O_4$ HCl (MW=533.12):

| Calcd: | C, 63.08; | H, 7.75; | N, 10.51; | Cl, 6.65. |
| Found: | C, 62.95; | H, 7.51; | N, 10.86; | Cl, 6.64. |

NMR for (D)Ala—$CH_3$=1.28δ($CD_3OD$) $[α]_D$−68.2° ($CH_3OH$).

Example 8

N-[(1,1-dimethylethoxy)carbonyl]-2,6-dimethyl-O-[[(phenylmethyl)amino]carbonyl]-D-tyrosyl-N-(3-phenylpropyl)-D-alaninamide.

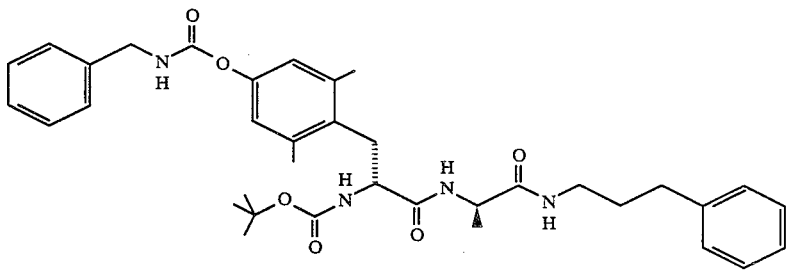

The title compound was prepared according to the method of Example 6 by substituting benzyl isocyanate in place of n-butylisocyanate. Unlike Example 6, the reaction was driven to completion by refluxing the reaction mixture for 36 hours.

Analysis for $C_{36}H_{46}N_4O_6$ (MW=630.79):

NMR for (D)Ala—$CH_3$=1.30δ($CD_3OD$) $[α]_D$+7.8°($CHCl_3$).

Example 9

2,6-dimethyl-O-[[(phenylmethyl)amino]carbonyl]-D-tyrosyl-N-(3-phenylpropyl)-D-alaninamide, monohydrochloride.

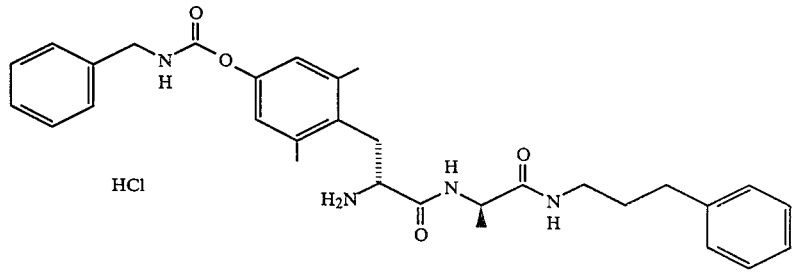

The product of Example 8 was reacted in glacial acetic acid with 6.8N HCl/dioxane according to the method described in Example 3 to produce the titled hydrochloride product.

Analysis for $C_{31}H_{38}N_4O_4$ HCl (MW=567.13):

| Calcd: | C, 65.65; | H, 6.93; | N, 9.88; | Cl, 6.25. |
| Found: | C, 65.28; | H, 6.72; | N, 9.74; | Cl, 6.20. |

NMR for (D)Ala—$CH_3$=1.29δ($CD_3OD$) $[α]_D$−53.5°($CH_3OH$).

Example 10

2,6-dimethyl-O-[(phenylamino)carbonyl]-L-tyrosyl-N-(3-phenylpropyl)-D-alaninamide, monohydrochloride.

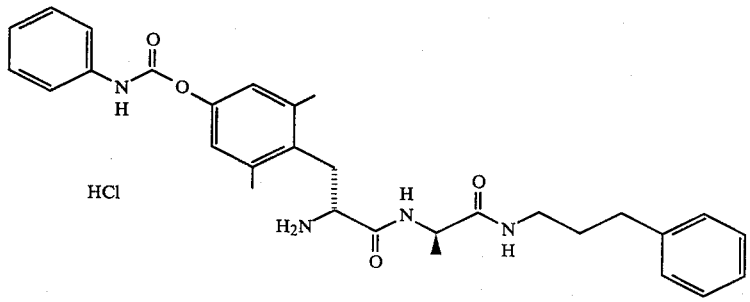

The Boc-precursor of the titled compound is prepared according to the method of Example 2 using the diastereomer, N[(1,1-dimethylethoxy)carbonyl]-2,6-dimethyl-L-tyrosyl-N-(3-phenylpropyl)-D-alaniamide, in place of its DL-tyrosine containing analogs. The resulting 2,6-dimethyl-O-[(phenylamino)carbonyl]-L-tyrosyl-N-(3-phenylpropyl)-D-alaninamide is then reacted with glacial acetic acid and 6.8N HCl-dioxane according to the method of Example 3 to produce the titled hydrochloride.

Example 11

O-[(butylamino)carbonyl]-2,6-dimethyl-L-tyrosyl-N-(3-phenylpropyl)-D-alaninamide, monohydrochloride.

The Boc-precursor of the titled compound is prepared by the method of Example 6 using N[(1,1-dimethylethoxy)carbonyl]-2,6-dimethyl-L-tyrosyl-N-(3-phenylpropyl)-D-alaninamide in place of its D-tyrosine containing analog. The resulting Boc-precursor is reacted with glacial acetic acid and 6.8N HCl-dioxane according to the method of Example 3 to produce the titled hydrochloride salt.

Example 12

2,6-dimethyl-O-[[(phenylmethyl)amino]carbonyl]-L-tyrosyl-N-(3-phenylpropyl)-D-alaninamide, monohydrochloride.

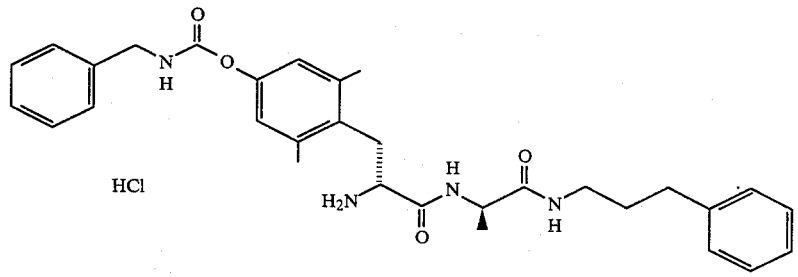

The Boc-precursor of the title compound is prepared according the method of Example 8 using N[(1,1-dimethylethoxy)carbonyl]-2,6-dimethyl-L-tyrosyl-N-(3-phenylpropyl)-D-alaninamide, in place of its D-tyrosine containing analog. The resulting Boc-precursor is reacted with glacial acetic acid and 6.8N HCl-dioxane according to the method of Example 3 to produce the titled hydrochloride.

Example 13

N-[(1,1-dimethylethoxy)carbonyl]-2,6-dimethyl-O-(phenoxycarbonyl)-L-tyrosyl-N-(3-phenylpropyl)-D-alaninamide.

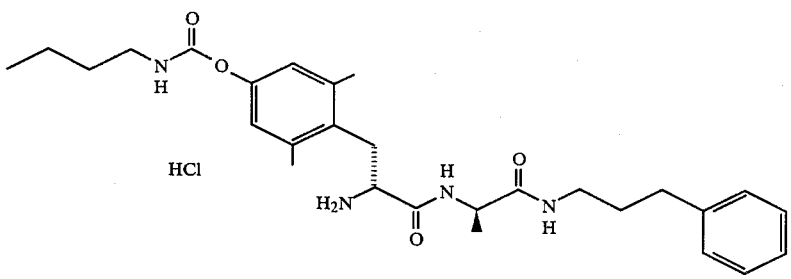

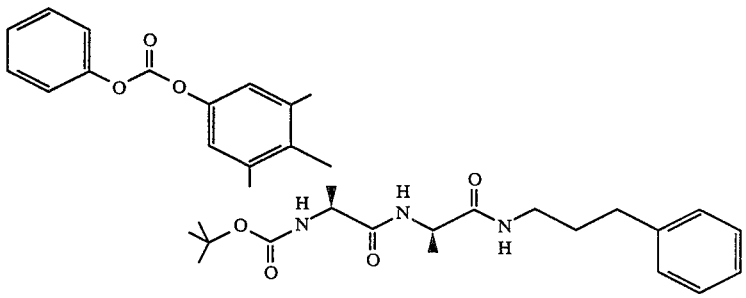

To N[(1,1-dimethylethoxy)carbonyl]-2,6-dimethyl-L-tyrosyl-N-(3-phenoxy propyl)-D-alaninamide dissolved in CH₂Cl₂, containing 2% DMF and cooled to 0° C. is added 1.1 equivalents of N-methylmorpholine. The reaction is then cooled to −20° C. and maintained under an argon atmosphere. Phenylchloroformate (1.1 equivalents) is then added to the stirred reaction mixture. The reaction mixture is permitted to slowly warm up to room temperature and stir overnight. The reaction mixture is then filtered through diatomaceous earth and the filtrate diluted with CH₂Cl₂. Afterwards, the diluted filtrate is washed with 0.5N KHSO₄ and H₂O, and the organic layer is separated. The CH₂Cl₂ is removed from the organic layer under reduced pressure leaving a residue. The residue is redissolved in ethyl acetate and then washed with H₂O and dried (Na₂SO₄). The ethyl acetate is removed under reduced pressure and the residue is chromatographed on silica gel to produce the titled compound.

Example 14

2,6-dimethyl-O-(phenoxycarbonyl)-L-tyrosyl-N-(3-phenylpropyl)-D-alaninamide, monohydrochloride.

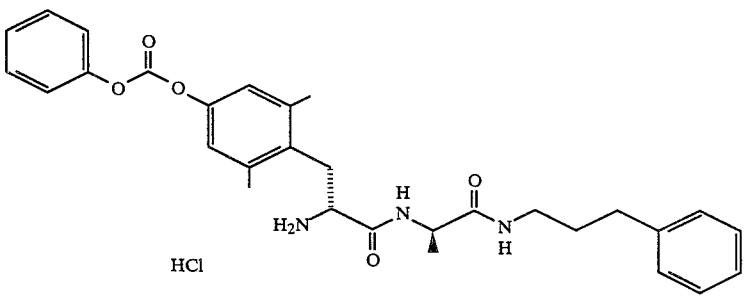

The product of Example 13 is dissolved in glacial acetic acid and reacted with 6.8N HCl-dioxane according to the method of Example 3 to produce the titled hydrochloride compound.

Example 15

N-[(1,1-dimethylethoxy)carbonyl]-2,6-dimethyl-O-[(phenylmethoxy)carbonyl]-L-tyrosyl-N-(3-phenylpropyl)-D-alaninamide.

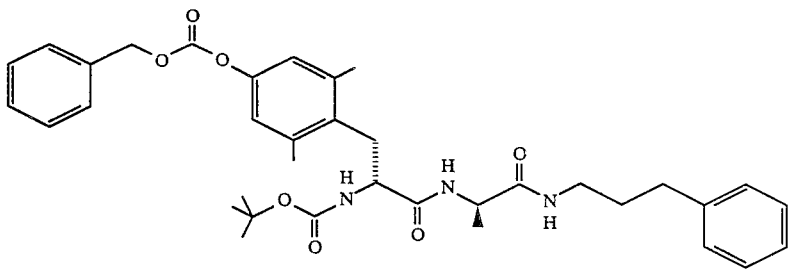

To N[(1,1-dimethylethoxy)carbonyl]-2,6-dimethyl-L-tyrosyl-N-(3-phenylpropyl)-D-alaninamide (1.0 g, 2.0 mmol) dissolved in 75 ml of CH₂Cl₂ and cooled to −20° C. was added 264 mg (0.3 mmol) of N-methylmorpholine. The reaction was then cooled to −78° C. and maintained under an argon atmosphere. Benzylchloroformate (445 mg, 2.5 mmol) was then added to the stirred reaction mixture. The reaction was allowed to slowly warm to room temperature an stir overnight. The mixture was then filtered and the filtrate diluted with CH₂CL₂ (150 ml). This filtrate was washed 3 times with 75 ml aliquots of 0.5N KHSO₄ and once with 75 ml of brine before it was dried over Na₂SO₄. The organic layer was then stripped of all solvent under reduced pressure to yield a pale yellow solid which by TLC was a mixture of product and starting material. This material was redissolved in 40 ml of CH₂CL₂ and then retreated with N-methylmorpholine and benzylchloroformate in a manner identical to the reaction disclosed above. This second reaction was worked up as described for the original reaction yield a pale yellow solid which was then triterated with hexane containing 5% diethylether to give 1.24 g of the titled product.
Analysis for $C_{36}H_{45}N_3O_7$ (MW=631.77):

| Calcd: | C, 68.44; | H, 7.18; | N, 6.65. |
|---|---|---|---|
| Found: | C, 68.37; | H, 7.32; | N, 6.60. |

NMR for (D)Ala—$CH_3$=1.03δ($CD_2Cl_2$)
$[α]_D$+22.2°($CHCl_3$).

Example 16

2,6-dimethyl-O-[(phenylmethoxy)carbonyl]-L-tyrosyl-N-(3-phenylpropyl)-D-alaninamide, monohydrochloride.

The product of Example 15 was dissolved in glacial acetic acid and reacted with 6.8N HCl/dioxane according to the method in Example 3 to produce the titled hydrochloride product.
Analysis for $C_{31}H_{38}N_3O_5Cl$ (MW=568.12):

| Calcd: | C, 65.54; | H, 6.74; | N, 7.40; | Cl, 6.24. |
|---|---|---|---|---|
| Found: | C, 65.18; | H, 6.76; | N, 7.41; | Cl, 6.23. |

NMR for (D)Ala—$CH_3$=0.96δ($CD_3OD$)
$[α]_D$+97.4°($CH_3OH$).

Example 17

N-[(1,1-dimethylethoxy)carbonyl]-2,6-dimethyl-O-[(2-propenyloxy)carbonyl]-L-tyrosyl-N-(3-phenylpropyl)-D-alaninamide.

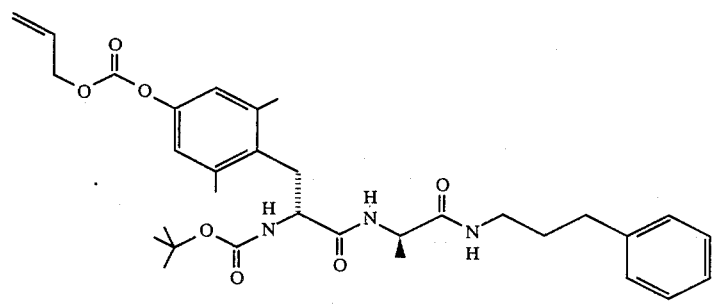

The title compound was prepared by the method of Example 15 substituting allychloroformate in place of benzylchloroformate.
Analysis for $C_{32}H_{43}N_3O_7$ (MW=581.71):

| Calcd: | C, 66.07; | H, 7.45; | N, 7.22. |
|---|---|---|---|
| Found: | C, 65.97; | H, 7.62; | N, 7.18. |

NMR for (D)Ala—$CH_3$=1.07δ($CD_2Cl_2$)

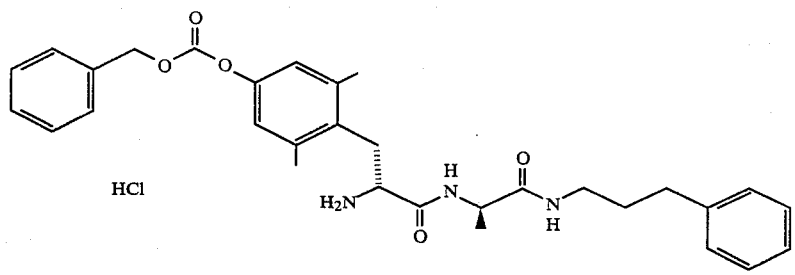

$[α]_D$+25.2°($CHCl_3$).

Example 18

2.6-dimethyl-O-[(2-propenyloxy)carbonyl]-L-tyrosyl-N-(3-phenylpropyl)-D-alaninamide, trifluoroacetate.

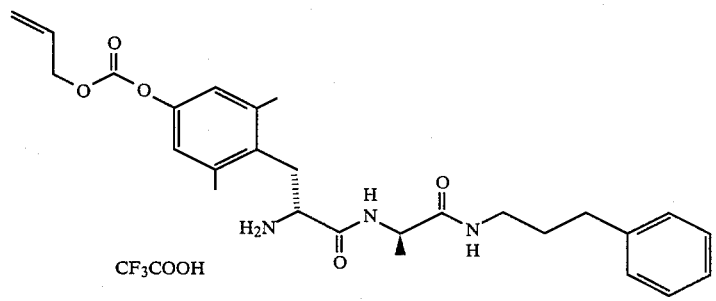

The product of Example 17 was converted into its trifluoroacetate salt by conventional methods well known in the art.
Analysis for $C_{29}H_{36}N_3O_7F_3$ (MW=595.62)

| Calcd: | C, 58.48; | H, 6.09; | N, 7.06; | F, 9.57. |
|---|---|---|---|---|
| | C, 58.72; | H, 6.09; | N, 7.10; | F, 9.54. |

NMR for (D)Ala—CH$_3$=1.04δ(CD$_3$OD) [α]$_D$+120.0°(CH$_3$OH).

Example 19

The DD analogs of Examples 14, 16, and 18 wherein the 2,6-dimethyltyrosine moiety in the final product is replaced by a 2,6-dimethyl-D-tyrosine moiety, are prepared by the methods of Examples 13 and 14, 15 and 16, and 17 and 18 respectively, by substituting Boc-2,6-dimethyl-D-tyrosyl-N-(3-phenylpropyl)-D-alaninamide for Boc-2,6-dimethyl-tyrosyl-N-(3-phenylpropyl)-D-alaninamide in Examples 13, 15, and 17, the DD analogs respectively being:

O-(phenoxycarbonyl)-2,6-dimethyl-D-tyrosyl-N-(3-phenylpropyl)-D-alaninamide, monohydrochloride;

2.6-dimethyl-O-[(phenylmethoxy)carbonyl]-D-tyrosyl-N-(3-phenylpropyl)-D-alaninamide, monohydrochloride; and 2,6-dimethyl-O-)[2-propenyloxy)carbonyl]-D-tyrosyl-N-(3-phenylpropyl)-D-alaninamide, hydrochloride.

What is claimed is:

1. A compound of the formula:

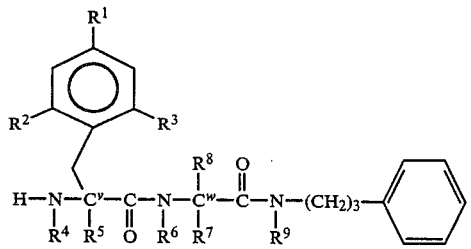

and the pharmaceutically acceptable acid addition salts thereof, wherein R$_1$ is

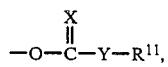

wherein X is oxygen or sulfur, Y is oxygen or nitrogen, and R$_{11}$ represents straight or branched chain lower alkenyl having 1-6 carbon atoms, or phenyl or benzyl; wherein R$^2$ and R$^3$ may be the same or different and represents straight or branched chain lower alkyl having 1-6 carbon atoms; wherein R$^4$-R$^9$ may be the same or different and represent hydrogen, or straight or branched chain lower alkyl having 1-6 carbon atoms; wherein C$^w$ is an asymmetric carbon atom when R$^7$ and R$^8$ are not the same and may be racemic or may have the D or L configuration; and wherein C$^v$ is an asymmetric carbon atom and may be racemic or having the D or L configuration.

2. A compound according to claim 1 of the formula:

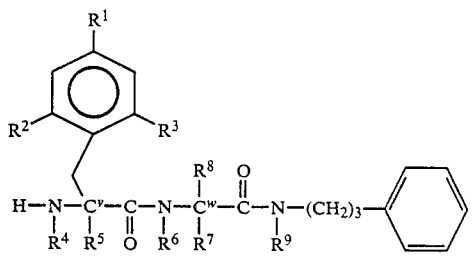

and the pharmaceutically acceptable addition salts thereof, wherein R$^1$ is

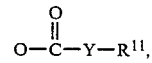

wherein Y is oxygen or nitrogen, and R$^{11}$ represents straight or branched chain lower alkenyl having 2-6 carbon atoms, or phenyl or benzyl; wherein R$^4$-R$^9$ may be the same or different and represents hydrogen, or straight or branched chain lower alkyl having 1-6 carbon atoms; wherein C$^w$ is an asymmetric carbon atom when R$^7$ and R$^8$ are not the same and may be racemic or may have the D or L configuration and wherein C$^v$ is an asymmetric carbon atom and may be racemic or have the D or L configuration.

3. A compound according to claim 1 of the formula:

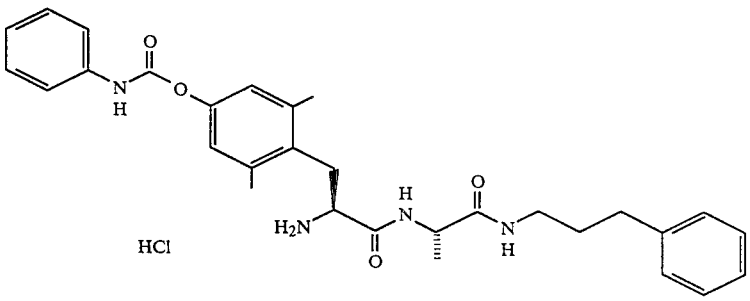

2,6-dimethyl-O-[(phenylamino)carbonyl]-L-tyrosyl-N-(3-phenylpropyl)-L-alaninamide, monohydrochloride.

4. A compound according to claim 1 of the formula:

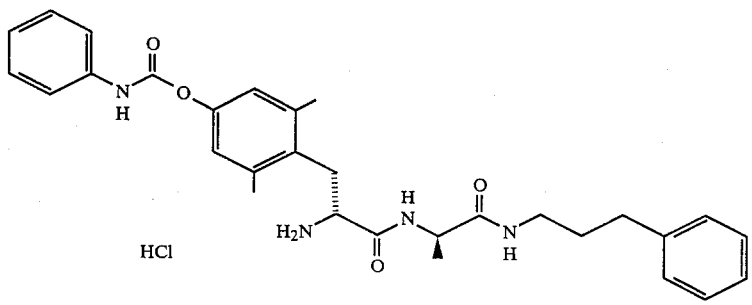

2,6-dimethyl-O-[(phenylamino)carbonyl]-D-tyrosyl-N-(3-phenylpropyl)-D-alaninamide, monohydrochloride.

5. A compound according to claim 1 of the formula:

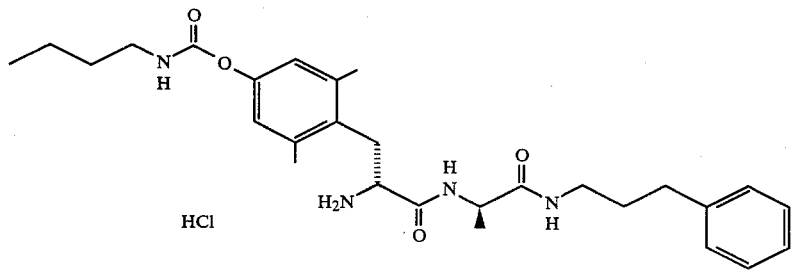

O-[(butylamino)carbonyl]-2,6-dimethyl-D-tyrosyl-N-(3-phenylpropyl)-D-alaninamide, monoydrochloride.

6. A compound according to claim 1 of the formula:

2,6-dimethyl-O-[[(phenylmethyl)amino]carbonyl]-D-tyrosyl-N-(3-phenylpropyl)-D-alaninamide, monohydrochloride.

7. A compound according to claim 1 of the formula:

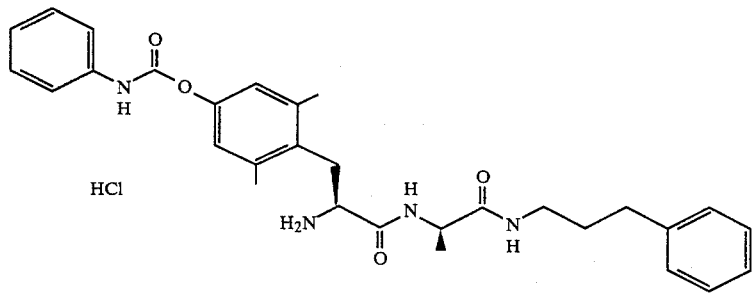

2,6-dimethyl-O-[(phenylamino)carbonyl]-L-tyrosyl-N-(3-phenylpropyl)-D-alaninamide, monohydrochloride.

8. A compound according to claim 1 of the formula:

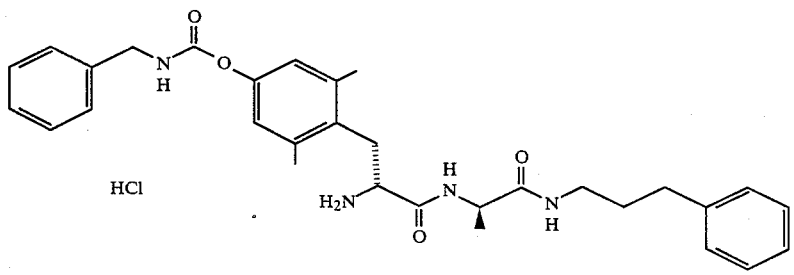

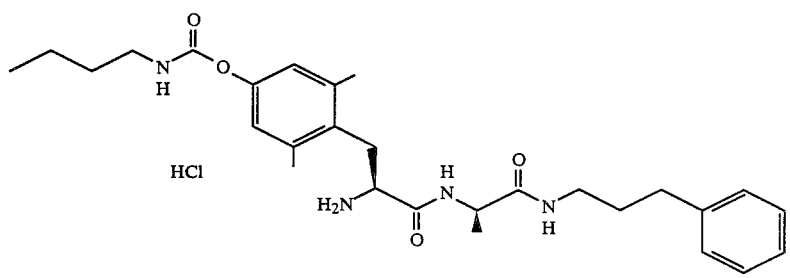

O-[(butylamino)carbonyl]-2,6-dimethyl-L-tyrosyl-N-(3-phenylpropyl)-D-alaninamide, monohydrochloride.

9. A compound according to claim 1 of the formula:

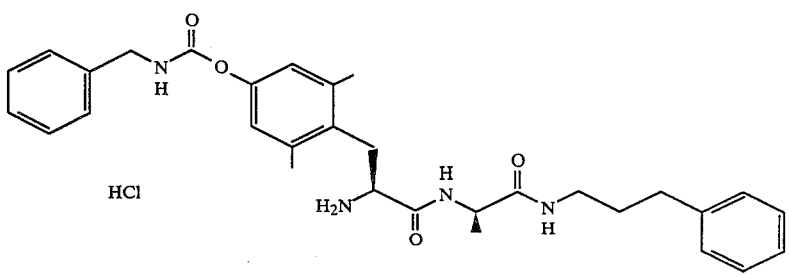

2,6-dimethyl-O-[[(phenylmethyl)amino]carbonyl]-L-tyrosyl-N-(3-phenylpropyl)-D-alaninamide, monohydrochloride.

10. A compound according to claim 1 of the formula:

2,6-dimethyl-O-(phenoxycarbonyl)-L-tyrosyl-N-(3-phenylpropyl)-D-alaninamide, monohydrochloride.

11. A compound according to claim 1 of the formula:

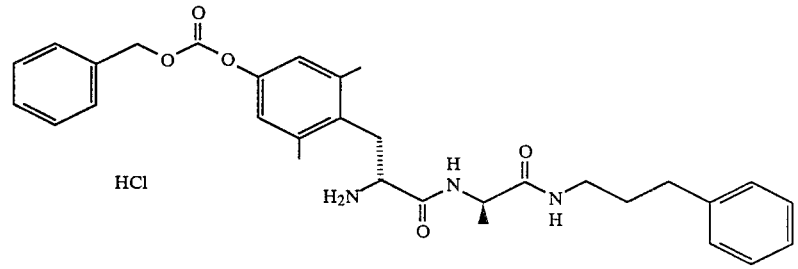

2,6-dimethyl-O-[(phenylmethoxy)carbonyl]-L-tyrosyl-N-(3-phenylpropyl)-D-alaninamide, monohydrochloride.

12. A compound according to claim 1 of the formula:

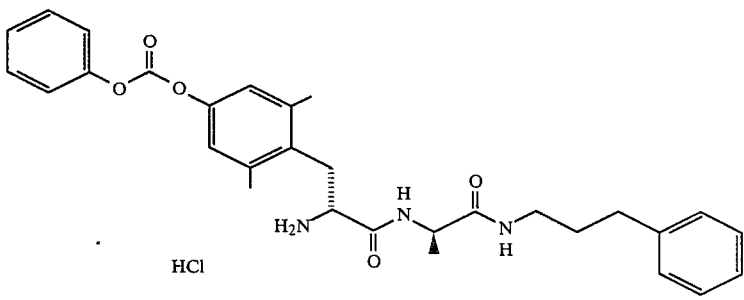

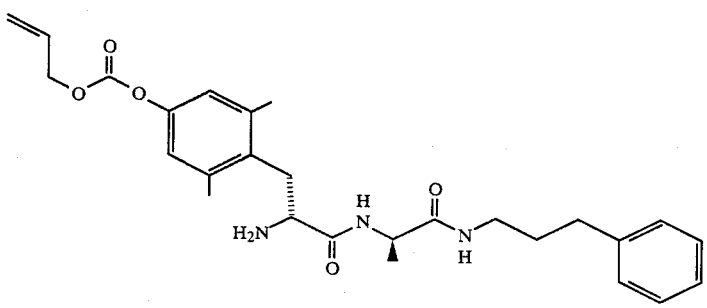

2,6-dimethyl-O-[2-propenyloxy)carbonyl]-L-tyrosyl-N-(3-phenylpropyl)-D-alaninamide, trifluoroacetate.

13. A compound according to claim 1 which is O-(phenoxycarbonyl)-2,6-dimethyl-D-tyrosyl-N-(3-phenylpropyl)-D-alaninamide, hydrochloride.

14. A compound according to claim 1 which is 2,6-dimethyl-O-[(phenylmethoxy)carbonyl]-D-tyrosyl-N-(3-phenylpropyl)-D-alaninamide, hydrochloride.

15. A compound according to claim 1 which is 2,6-dimethyl-O-[(2-propenyloxy)carbonyl]-D-tyrosyl-N-(3-phenylpropyl)-D-alaninamide, hydrochloride.

* * * * *

UNITED STATES PATENT AND TRADEMARK OFFICE
CERTIFICATE OF CORRECTION

PATENT NO. : 4,797,470
DATED : January 10, 1989
INVENTOR(S) : Pitzele, et al

It is certified that error appears in the above-identified patent and that said Letters Patent is hereby corrected as shown below:

On the title page and column 1, lines 1 and 2, "N-TERMINALLY SUBSTITUTED TYROSYL ALANINE" should read --O-SUBSTITUTED TYROSYL DIPEPTIDE AMIDES --.

Column 7, line 55, "plug" should read --plus--.

Column 10, line 24 "dimentyl" should read --dimethyl--.

Column 13, the first structure, Example 10, that portion of the structure reading Column 13, the second structure, Example 11, that portion of the structure reading

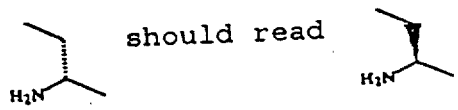

UNITED STATES PATENT AND TRADEMARK OFFICE
CERTIFICATE OF CORRECTION

PATENT NO. : 4,797,470
DATED : January 10, 1989
INVENTOR(S) : Pitzele, et al

It is certified that error appears in the above-identified patent and that said Letters Patent is hereby corrected as shown below:

Column 14, the first structure, Example 12, that portion of the structure reading should read Column 16, the first structure, Example 15, that portion of the structure reading

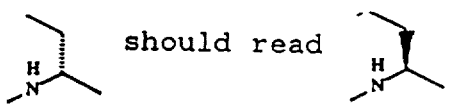 should read

Column 17, the first structure, Example 16, that portion of the structure reading

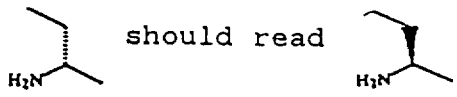 should read

UNITED STATES PATENT AND TRADEMARK OFFICE
CERTIFICATE OF CORRECTION

PATENT NO. : 4,797,470
DATED : January 10, 1989
INVENTOR(S) : Pitzele, et al

Page 3 of 4

It is certified that error appears in the above-identified patent and that said Letters Patent is hereby corrected as shown below:

Column 18, the first structure, Example 17, that portion of the structure reading should read Column 18, the second structure, Example 18, that portion of the structure reading

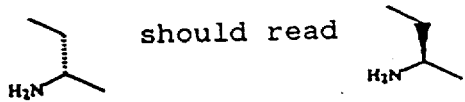 should read

Column 23, the third structure, Claim 10, that portion of the structure reading

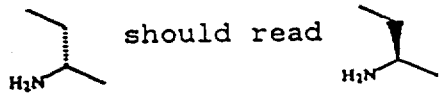 should read

UNITED STATES PATENT AND TRADEMARK OFFICE
CERTIFICATE OF CORRECTION

PATENT NO. : 4,797,470

DATED : January 10, 1989

INVENTOR(S) : Pitzele, et al

It is certified that error appears in the above-identified patent and that said Letters Patent is hereby corrected as shown below:

Column 24, the first structure, Claim 11, that portion of the structure reading

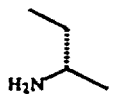 should read 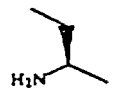

Column 25, the first structure, Claim 12, that portion of the structure reading

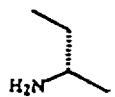 should read 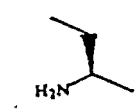

Signed and Sealed this

Fourth Day of December, 1990

Attest:

HARRY F. MANBECK, JR.

*Attesting Officer*          *Commissioner of Patents and Trademarks*